Figure 1:
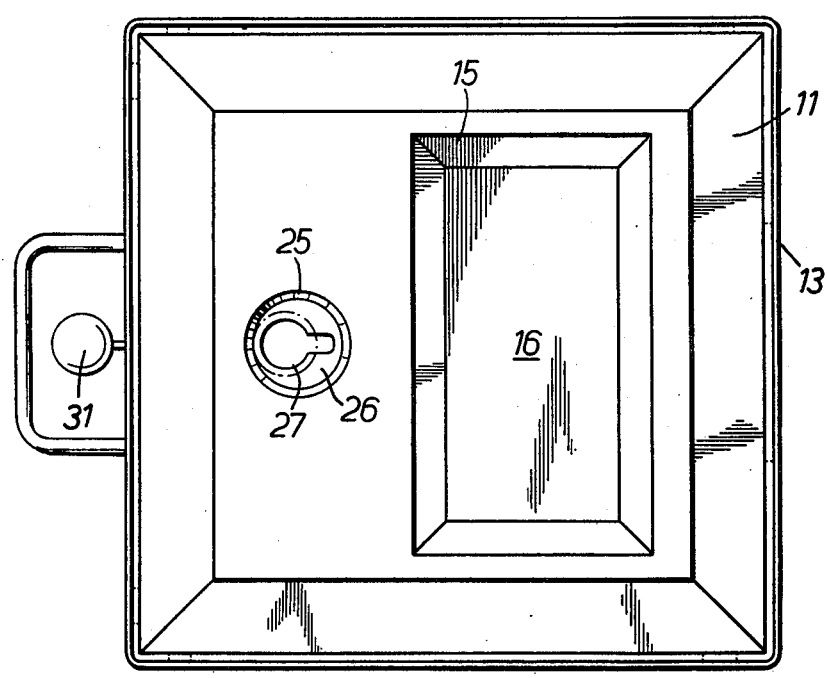

United States Patent [19]
Harris et al.

[11] 4,453,648
[45] Jun. 12, 1984

[54] DISPOSAL BIN

[75] Inventors: John Harris, Newport; John E. Anthony, Llanyrafon, both of Wales

[73] Assignee: Frontier Plastics (South Wales) Limited, Crosskeys, England

[21] Appl. No.: 323,264

[22] Filed: Nov. 19, 1981

[30] Foreign Application Priority Data

Nov. 19, 1980 [GB] United Kingdom ............... 8037154

[51] Int. Cl.³ .................... B65D 43/14; B65D 45/00; B65D 51/04
[52] U.S. Cl. .................................. 220/324; 206/370; 220/1 T; 220/214; 292/327
[58] Field of Search ................... 206/63.3, 63.5, 370; 220/1 T, 214, 324, 375; 232/41 D; 292/288, 307 R, 327

[56] References Cited

U.S. PATENT DOCUMENTS

| | | | |
|---|---|---|---|
| 79,801 | 7/1868 | Adams | 292/327 |
| 414,635 | 11/1889 | Gardner | 292/307 R |
| 1,169,606 | 1/1916 | Blank et al. | 220/1 T |
| 1,765,345 | 6/1930 | Raphael | 292/307 R |
| 4,032,037 | 6/1977 | Dubery et al. | 220/1 T |
| 4,371,092 | 2/1983 | Teague | 220/1 T |

FOREIGN PATENT DOCUMENTS 2740335 3/1979 Fed. Rep. of Germany ..... 206/63.5

*Primary Examiner*—George E. Lowrance
*Assistant Examiner*—Jimmy G. Foster
*Attorney, Agent, or Firm*—Young & Thompson

[57] ABSTRACT

A disposable container for used items of medical equipment such as hypodermic needles, has an entry chute in its upper wall and an internal self-closing door flap which will swing downwards to allow an object to enter and swing upwards under gravity to close the chute. When the container is full a locking probe is inserted through a hole in the top wall, where it is locked by barbs and presses down a lever attached to the door to hold the door positively closed without any risk of accidental opening.

4 Claims, 2 Drawing Figures

DISPOSAL BIN

This invention relates to a bin or container designed to receive items for disposal and is particularly though not exclusively applicable to a container for used items of medical equipment.

It is normal practice in hospitals, for example, to provide disposal boxes to receive different types of medical refuse for disposal. One special class of items for disposal is commonly referred to as "Sharps" and includes items such as used hypodermic needles, or broken glass phials or pharmaceutical containers. After use these articles may be potentially very dangerous, if not unsanitary or unhygenic. Some of the articles may, for example, be coated with blood or contaminated in other ways. Other objects may still carry quantities of drugs and in addition there is the physical danger of injury to hands or fingers from the presence of sharp points or edges. Attempts have been made to provide disposal containers for such items but existing containers for the purpose suffer from various disadvantages and it is an object of this present invention to provide an improved container which will meet some of the requirements and satisfy some of the present problems.

Broadly stated, the invention consists in a container for used items of medical equipment, or other refuse, having an entrance opening at or near the top, a movable door biassed to a position closing the entrance and locking means for irreversibly holding the door closed.

According to a preferred feature of the invention the locking means is operable externally from outside the container. The locking means may include an irreversible catch or detent, and in a particular preferred construction it includes a probe which can be inserted through an aperture in a container and will close the aperture and become locked therein when inserted.

According to another preferred feature of the invention the container has a transparent window. This provides a number of important advantages. It is possible to observe when the container is nearly full so that it can be removed and replaced, any mistaken or accidental disposal of an object which ought not to have been placed in the container can also be observed, and importantly, a person using the container can observe externally whether there are any dangerous sharp points or cutting edges close to the entrance.

In any case, the container is preferably provided with a duct or chute extending partly inwards into the body of the container. Thus, if the container should accidentally be overturned, it is most unlikely that any of the contents will escape. The container is also preferably provided with a device for removing needles from syringes, associated with an aperture to allow the needle to fall into the container.

To hold the door irreversibly closed it is convenient to use a probe or other stem inserted through a small aperture in the container wall to engage a lever attached to the door. After being inserted the probe will then lock in position in the aperture and form a seal, to prevent the contents escaping. This aperture may also act as the entry for hypodermic needles and to prevent the needles or other objects from accidentally engaging the door lever this lever is preferably provided with a sharp operating point or knife edge to be engaged by the probe.

Figure 2:
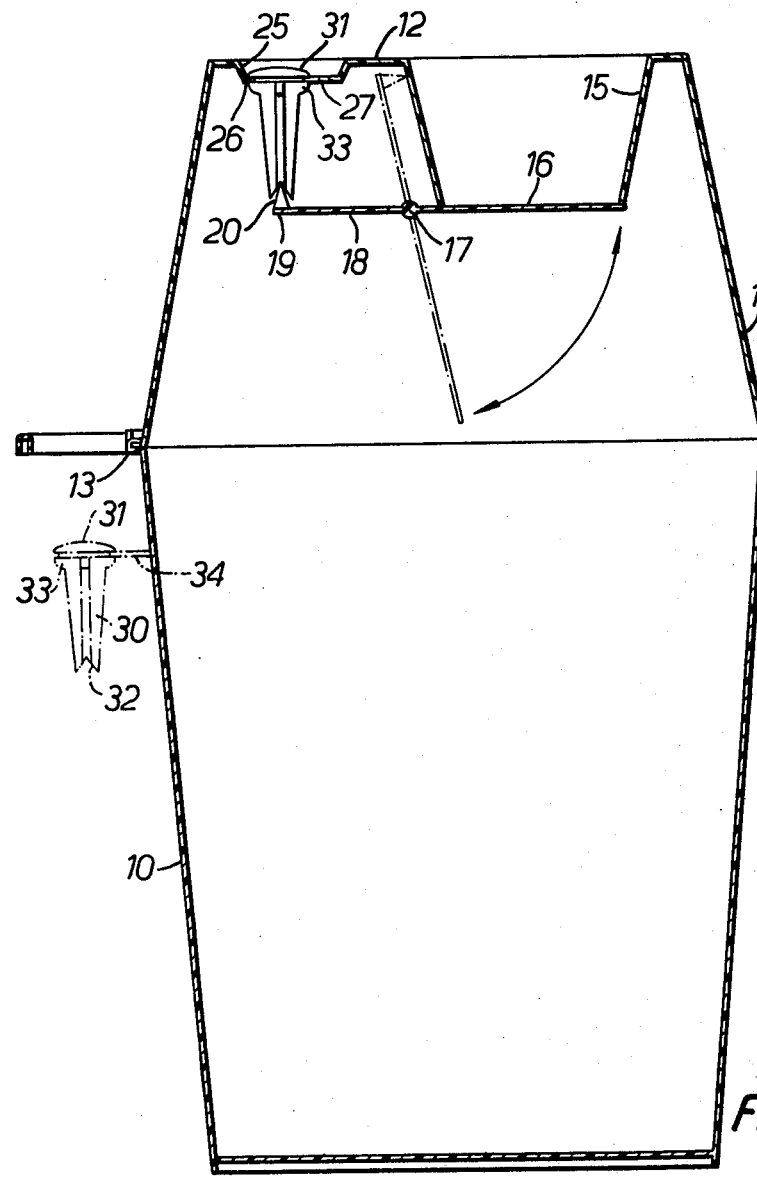

The invention may be performed in various ways and one specific embodiment, with a number of possible modifications, will now be described by way of example with reference to the accompanying drawings in which:

FIG. 1 is a plan view of one form of disposal container according to the invention, and FIG. 2 is a sectional side elevation through the container of FIG. 1.

In this example the disposal container comprises a small bin formed in synthetic plastics material and generally square or rectangular in plan. There is a base portion 10 with four side walls and a bottom wall, and an upper cover or lid 11 also with four inward tapering side walls and a generally flat top wall 12. The cover is formed separately from the base and is permanently and irremovably attached by a snap-acting, flange fitting 13. The cover is formed in a translucent plastics whereas the base is preferably opaque.

Offset laterally from the centre of the cover 11 is an inwardly tapering chute 15 providing an entrance to the container at its lower end or mouth. This is normally closed by a transparent hinged door 16 which is mounted on a horizontal hinge or pivot axis 17 and has a laterally projecting arm or stirrup 18 on the opposite side of the hinge pivot. At the remote end of this lever 18 is a transverse bar 19 provided with a sharp knife edge ridge 20. The door 16, lever 18 and bar 19 are so balanced that normally the door 16 is held upwards against the mouth of the entrance chute 15. When an object to be disposed of is dropped through the chute however the door 16 automatically opens downwards and then re-closes.

One of the more common objects to be disposed of is a hypodermic needle. For this special item the container is formed with a small depression 25 in its top wall with a depressed bottom wall 26 formed with a keyhole slot 27. The slot will accept the standard sized hypodermic needle and then by drawing the needle into the narrow part of the slot and pulling back on the syringe, the needle will be detached and will fall through into the body of the container. In doing so it may accidentally impinge on the knife edge bar 20 but naturally will not be retained.

When the container is substantially full and is to be disposed of, it is necessary to close the top door 16 permanently to prevent the contents escaping. For this purpose the body of the container is provided with an external operating probe 30 which is conveniently moulded integral with the body and attached to the side wall by a short easily broken stalk 34. The probe can easily be removed from the body and it comprises a cruciform stem with a slightly enlarged upper head 31, and a notch 32 at the lower end of the stem. By inserting the stem through the opening in the depressed wall 26 it can be made to engage the knife edge 20 thus locking the lever 18 to hold the door 16 firmly against the entrance mouth of the chute. Four barbs or detents 33 on the side surfaces of the stem pass through the aperture in the wall 26, and spring outwards to prevent the stem being withdrawn. The head on the stem then occupies and substantially fills the depression 25 which makes even deliberate removal of the stem extremely difficult.

We claim:

1. A hygienic container for refuse, comprising a body including an inwardly directed chute defining an entrance opening adjacent the top, a movable door pivotally mounted on a pivot located within said body, and biased upwards to a closed position closing the entrance at the inner end of said chute, said door having a projection extending beyond said pivot, and locking means operable from outside said container, said locking means comprising a plug having an enlarged head and a body, the container having an aperture through which the body but not the head of the plug is insertable, the container and the plug having coacting structure whereby when the plug is inserted in the aperture, the plug becomes locked in the aperture and the head of the probe closes the aperture and the body of the plug engages the said projection of said door for irreversibly holding the door closed.

2. A container according to claim 1 in which an upper part of said container is transparent.

3. A container according to claim 1, including a device for removing needles from syringes, associated with said aperture to allow the needle to fall into the container.

4. A container according to claim 1, wherein said projection from said door is formed with a pressure element having a sharp upper profile, and the end of said plug body engages said pressure element to hold said door closed.

* * * * *